United States Patent [19]
Shahidi

[11] Patent Number: 5,688,491
[45] Date of Patent: *Nov. 18, 1997

[54] ORAL COMPOSITIONS

[75] Inventor: Hooman Shahidi, Cincinnati, Ohio

[73] Assignee: The Procter & Gamble Company, Cincinnati, Ohio

[*] Notice: The term of this patent shall not extend beyond the expiration date of Pat. No. 5,389,360.

[21] Appl. No.: 634,030

[22] Filed: Apr. 17, 1996

Related U.S. Application Data

[63] Continuation of Ser. No. 306,868, Sep. 15, 1994, abandoned.

[51] Int. Cl.$^6$ ............................. A61K 7/16; A61K 7/18
[52] U.S. Cl. ................................. 424/49; 424/52
[58] Field of Search .......................... 424/49–58

[56] References Cited

U.S. PATENT DOCUMENTS

| | | | |
|---|---|---|---|
| 3,655,868 | 4/1972 | Vagenius | 424/54 |
| 4,112,066 | 9/1978 | Hussein | 424/48 |
| 4,170,632 | 10/1979 | Wagenknecht et al. | 424/48 |
| 4,180,473 | 12/1979 | Maurer et al. | 252/182 |
| 4,278,610 | 7/1981 | Maurer et al. | 260/438.1 |
| 4,332,791 | 6/1982 | Raaf et al. | 424/52 |
| 4,339,429 | 7/1982 | Raaf et al. | 424/49 |
| 4,339,432 | 7/1982 | Ritchey et al. | 424/54 |
| 4,416,867 | 11/1983 | Ritchey et al. | 424/49 |
| 4,425,325 | 1/1984 | Ritchey et al. | 424/54 |
| 4,652,444 | 3/1987 | Maurer | 424/49 |
| 4,693,888 | 9/1987 | Miyahara et al. | 424/49 |
| 4,708,864 | 11/1987 | Maurer | 424/49 |
| 4,795,628 | 1/1989 | Afseth | 424/54 |
| 4,806,340 | 2/1989 | Gaffar et al. | 424/52 |
| 4,824,661 | 4/1989 | Wagner | 424/52 |
| 4,863,898 | 9/1989 | Ashmead et al. | 514/6 |
| 4,908,211 | 3/1990 | Paz | 424/440 |
| 4,985,236 | 1/1991 | Ibrahim et al. | 424/52 |
| 5,037,634 | 8/1991 | Williams et al. | 424/49 |
| 5,075,291 | 12/1991 | Duross | 514/60 |
| 5,094,842 | 3/1992 | Riley | 424/52 |
| 5,270,031 | 12/1993 | Lim et al. | 424/49 |
| 5,286,479 | 2/1994 | Garlich et al. | 424/54 |
| 5,292,538 | 3/1994 | Paul et al. | 426/74 |
| 5,298,237 | 3/1994 | Fine | 424/49 |
| 5,389,360 | 2/1995 | Mobley et al. | 424/49 |

FOREIGN PATENT DOCUMENTS

| | | | |
|---|---|---|---|
| 4123450 | 7/1991 | Denmark | A61K 7/16 |
| 0309414 | 3/1989 | European Pat. Off. | A23G 3/30 |
| 0508524 | 10/1992 | European Pat. Off. | A61K 33/30 |
| 0529212 | 3/1993 | European Pat. Off. | A61K 7/16 |
| 0549027 | 6/1993 | European Pat. Off. | A61K 7/16 |
| 79 42723 | 8/1976 | Germany . | |
| 212413 | 2/1989 | Japan | A61K 7/16 |

OTHER PUBLICATIONS

"The Effect of Sugar Alcohols on plaque and saliva level of *Streptococcus mutans*", pp. 125–135, Swedish Dental Journal, vol. 8 (1984).
Lion Corp JPN. 02212413 (Aug. 23, 1990) (Derwent).
Sokolova et al C.A. 79: 118887 (1973).
Duross C.A. 115:166664 of can. 20300670 (Aug. 23, 1991).
Bourne et al C.A. 74: 88250(1971).

*Primary Examiner*—Shep K. Rose
*Attorney, Agent, or Firm*—Mary Catherine Poland; Douglas C. Mohl; David K. Dabbiere

[57] ABSTRACT

Disclosed are oral compositions such as toothpastes, mouthrinses, liquid dentifrices, lozenges and gums containing copper bis-glycinate.

9 Claims, No Drawings

ORAL COMPOSITIONS

This is a continuation of application Ser. No. 08/306,868, filed on Sep. 15, 1994, now abandoned.

TECHNICAL FIELD

The present invention relates to oral compositions which provide anticaries, antiplaque and antigingivitis benefits as well as being effective against other anaerobic infections of the mouth.

BACKGROUND OF THE INVENTION

Plaque induced diseases, including periodontitis and gingivitis, are believed to involve anaerobic bacterial infections. Periodontal disease affects the periodontium, which is the investing and supporting tissue surrounding a tooth (i.e., the periodontal ligament, the gingiva, and the alveolar bone). Gingivitis and periodontitis are inflammatory disorders of the gingiva and the periodontal ligament, respectively. Gingivosis and periodontosis are more severe conditions involving degenerative disorders of the tissue. Combinations of inflammatory and degenerative conditions are termed periodontitis complex.

Periodontal disease is a major cause of tooth loss in adults. Tooth loss from periodontal disease is a significant problem beginning at age 35, but even by age 15 it is estimated that about 4 out of 5 persons already have gingivitis and 4 out of 10 have periodontitis.

While good oral hygiene, as achieved by brushing the teeth with a cleansing dentifrice, may help reduce the incidence of periodontal disease, it does not necessarily prevent or eliminate its occurrence. This is because microorganisms contribute to both the initiation and progress of periodontal disease. Thus, in order to prevent or treat periodontal disease, these microorganisms must be suppressed by some means other than simple mechanical scrubbing. Towards this end, there has been a great deal of research aimed at developing therapeutic dentifrices, mouthwashes, and methods of treating periodontal disease which are effective in suppressing these microorganisms.

The use of copper compounds in oral products is disclosed in a number of references. One such reference is U.S. Pat. No. 4,332,791, issued Jun. 1, 1982 to Raaf et al. Raaf et al. describe combinations containing copper salts in dentifrice compositions employing a silica abrasive.

Another reference disclosing copper compounds is U.S. Pat. No. 4,652,444, issued Mar. 14, 1987, to Maurer. The specific copper compound disclosed is mono copper citrate which releases copper in accordance with a sigmoidally shaped curve.

Similarly, xylitol's usefulness in oral care compositions has been disclosed in DE 2606533, published Aug. 26, 1976, to Hoffman LaRoche. This reference describes xylitol's value in both the treatment and prevention of dental caries. Additionally, xylitol's value as an antiplaque agent has been described in Loesche, Grossman, Earnest and Corpron, *The Effect of Chewing Xylitol Gum on Plaque and Saliva Levels of Streptococcus Mutans*, 108 J.A.D.A. 587 (1984).

In spite of the many disclosures in the antiplaque/antigingivitis area, the need for improved products still exists. The present inventor has found that the combination of copper bis-glycinate and xylitol results in a new composition providing improved performance against diseases of the oral cavity such as plaque, gingivitis and periodontitis.

It is therefore an object of the present invention to provide improved products containing copper bis-glycinate and xylitol.

It is a further object of the present invention to provide more effective products for preventing and treating dental caries and other diseases of the oral cavity.

It is still a further object to provide methods for preventing and treating dental carries and other diseases of the oral cavity.

It is also an object of the present invention to provide products which are effective against bad breath.

These and other objects will become readily apparent from the disclosure which follows.

All percentages and ratios used herein are by weight unless otherwise specified. Also, all measurements referred to herein are made at 25° C. in the composition unless otherwise specified.

SUMMARY OF THE INVENTION

The present invention embraces oral compositions comprising:

(a) a safe and effective amount of xylitol;

(b) a safe and effective amount of copper bis-glycinate; and (c) a pharmaceutically acceptable carrier.

Preferably, the ratio of xylitol to copper bis-glycinate is from about 10,000 to 1 to about 1 to 10.

The present invention further encompasses a method for treating diseases of the oral cavity using the specified compositions.

By "oral compositions" as used herein means a product which in the ordinary course of usage is not intentionally swallowed for purposes of systemic administration of particular therapeutic agents, but is rather retained in the oral cavity for a time sufficient to contact substantially all of the dental surfaces and/or oral tissues for purposes of oral activity.

By "safe and effective amount" as used herein means sufficient amount of material to provide the desired benefit while being safe to the hard and soft tissues of the oral cavity.

By the term "comprising", as used herein, is meant that various additional components can be conjointly employed in the compositions of this invention as long as the materials perform their intended functions.

By the term "pharmaceutically acceptable carrier", as used herein, is meant a suitable vehicle which can be used to apply the present actives in the oral cavity.

DETAILED DESCRIPTION OF THE INVENTION

The essential as well as optional components of the compositions of the present invention are described in the following paragraphs.

ESSENTIAL COMPONENTS

Xylitol

One essential component of the present invention is xylitol. Xylitol, a monosaccharide polyhydric alcohol, occurs transiently as an intermediate product of D-glucose metabolism via glucuronic conjugation in the liver and is well known as a sucrose substitute. Xylitol is synthesized by reduction of xylose. Xylose is widely distributed in plant materials as the polymerized component of xylan. In its stable form, xylitol is a crystalline substance appearing as either orthorhombic needles or prisms. Xylitol differs from other monosaccharide, polyhydric alcohol sugar substitutes in that it is a pentitol with a 5-carbon-atom backbone; this is opposed to the more common hexitols, such as sorbitol and mannitol, which have a 6-carbon backbone. Xylitol is generally known as a tooth-preserving or non-cariogenic sugar substitute suitable for use in a wide variety of comestible products. It has been ascertained that xylitol neither encourages the growth of cariogenic bacteria nor lend itself to degradation by such organisms.

Xylitol is incorporated in the present invention at levels of about 0.05% to about 80%, preferably from about 20% to about 70%, more preferably from about 40% to about 60%.

Additional monosaccharide polyhydric alcohols can be used along with the xylitol. Preferred optional polyhydric alcohols include sorbitol and mannitol.

Copper bis-Glycinate

Another essential component of the present invention is Copper bis-glycinate. Copper bis-glycinate can be purchased as the salt and has the structural formula:

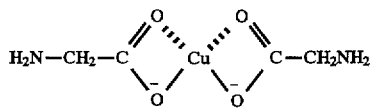

Copper bis-glycinate can also be formed in-situ by using appropriate salts of copper and glycine. Suitable copper compounds which supply copper ions are, in principle, all copper compounds being toxicologically harmless, compatible with mucous membranes and, to some extent, water-soluble.

The following inorganic copper salts may be used: Copper chloride, $CuCl_2$, and the dihydrate thereof, copper fluoride, $CuF_2$ and the dihydrate thereof, copper fluorosilicate, $CuSiF_6$, and the hexahydrate thereof, copper sulphate, $CuSO_4$, and the pentahydrate thereof; copper nitrate and the tri- and hexa-hydrates thereof; and also less popular copper salts, such as copper bromide, $CuBr_2$; copper metaborate, $Cu(BO_2)_2$; copper bromate, $Cu(BrO_3)_2$; copper chlorate; $Cu(Cl_3)_2$, $6-H_2O$; copper iodate $Cu(IO_3)_2$, and copper fluorophosphate, $CuPO_3F$.

Suitable sources of glycine besides glycine itself include sodium glycinate, potassium glycinate and glycine hydrochloride.

"Copper bis-glycinate" as the term is used herein includes ratios of copper and glycine differing somewhat from one part copper to two parts glycine. The ratios of copper to glycine which are most useful herein are as follows:

Preferred about 1:1.5 to about 1:3.5;

More preferred about 1:1.8 to about 1:3.0; and

Most preferred about 1:1.8 to about 1:2.4.

Copper bis-glycinate is used in an amount sufficient to provide from about 1 to about 8000, preferably from about 25 to about 6000, most preferably from about 50 to about 4000 ppm copper ions. For dentifrices the preferred levels are from about 200 to about 8000 ppm, more preferably from about 400 to about 6000 ppm, and most preferably from about 800 to about 4000 ppm. For rinses the levels are preferably from about 25 to about 1000 ppm, more preferably from about 50 to about 750 ppm, and most preferably from about 100 to about 500 ppm. For lozenges and chewing gums levels as low as about 1 ppm copper are effective.

Pharmaceutically Acceptable Carrier

The carrier for the components of the present compositions can be any vehicle suitable for use in the oral cavity. Such carriers include the usual components of mouthwashes, toothpastes, tooth powders, prophylaxis pastes, lozenges, chewing gums and the like and are more fully described hereinafter. Chewing gums, dentifrices and mouthwashes are the preferred systems.

Water is optionally present in the compositions of this invention. Water employed in the preparation these compositions should preferably be deionized and free of organic impurities. Water generally comprises from about 10% to 50%, preferably from about 20% to 40%, by weight of the compositions herein. These amounts of water include the free water which is added plus that which is introduced with other materials such as with sorbitol.

Another preferred nonessential component of the present invention is a cooling agent or a combination of cooling agents. Suitable cooling agents are those described in U.S. Pat. No. 4,136,163, Jan. 23, 1979, to Watson et al., U.S. Pat. Nos. 4,032,661 and 4,230,688, Jun. 28, 1977 and Oct. 28, 1980, respectively, to Rowsell et al. and U.S. Pat. No. 5,266,592, Nov. 30, 1993 to Grub et al., all of which are herein incorporated by reference. Particularly preferred cooling agents are N-ethyl-p-menthane-3-carboxamide (WS-3 supplied by Sterling Organics), taught by the above incorporated U.S. Pat. No. 4,136,163 and N,2,3-trimethyl-2-isopropyl-butanamide which is commercially available as WS-23 from Wilkinson Sword Limited and taught by the above incorporated U.S. Pat. No. 4,230,688. Another particularly preferred cooling agent is 3-1-menthoxypropane 1,2-diol (TK-10 supplied by Takasago Perfumery Co., Ltd., Tokyo, Japan). This material is described in detail in U.S. Pat. No. 4,459,425, Jul. 10, 1984 to Amano et al. and incorporated herein by reference.

It is also common to have a water-soluble fluoride compound present in compositions herein in an amount sufficient to give a fluoride ion concentration in the composition at 25° C., and/or when it is used of from about 0.0025% to about 5.0% by weight, preferably from about 0.005% to about 2.0% by weight, to provide additional anticaries effectiveness. A wide variety of fluoride ion-yielding materials can be employed as sources of soluble fluoride in the present compositions. Examples of suitable fluoride ion-yielding materials are found in U.S. Pat. No. 3,535,421, Oct. 20, 1970 to Briner et al. and U.S. Pat. No. 3,678,154, Jul. 18, 1972 to Widder et al., both being incorporated herein by reference. Representative fluoride ion sources include: stannous fluoride, sodium fluoride, potassium fluoride, sodium monofluorophosphate and many others. Stannous fluoride and sodium fluoride are particularly preferred, as well as mixtures thereof.

Another optional ingredient is a humectant. Humectants are well known in the art. The humectant may be a single agent or a mixture of compatible humectants In the present invention, suitable humectants include glycerin, sorbitol and mannitol as well as other polyhydroxy alcohols. While it is feasible to use a single humectant, the preferred embodiment incorporates a combination of humectants. Humectants provide from about 15% to about 70 and most preferably from about 5% to about 55% of the herein described invention. The preferred humectants include glycerin and/or sorbitol.

The abrasive polishing material contemplated for use in the compositions of the present invention can be any material which does not excessively abrade dentin and does not provide calcium ions which may precipitate with, for example, the fluoride ions provided from stannous fluoride. These include, for example, silicas including gels and precipitates, insoluble sodium polymetaphosphate, hydrated alumina, and resinous abrasive materials such as particulate condensation products of urea and formaldehyde, and others such as disclosed by Cooley et al. in U.S. Pat. No. 3,070,510, Dec. 25, 1962, incorporated herein by reference. Mixtures of abrasives may also be used. Abrasives such as calcium carbonate, calcium phosphate and regular calcium pyrophosphate are not preferred for use in the present compositions since they provide calcium ions which can complex F—.

Silica dental abrasives, of various types, can provide the unique benefits of exceptional dental cleaning and polishing performance without unduly abrading tooth enamel or dentin. Silica abrasive materials are also exceptionally compatible with sources of soluble fluoride. For these reasons they are preferred for use herein.

The silica abrasive polishing materials useful herein, as well as the other abrasive, generally have an average particle size ranging between about 0.1 and 30 microns, preferably 5 and 15 microns. The silica abrasive can be precipitated silica or silica gels such as the silica xerogels described in Pader et al., U.S. Pat. No. 3,538,230, issued Mar. 2, 1970 and DiGiulio, U.S. Pat. No. 3,862,307, Jun. 21, 1975 both incorporated herein by reference. Preferred are the silica xerogels marketed under the tradename "Syloid" by the W. R. Grace & Company, Davison Chemical Division. Preferred precipitated silica materials include those marketed by the J. M. Huber Corporation under the tradename, "Zeodent", particularly the silica carrying the designation "Zeodent 119". These silica abrasives are described in U.S. Pat. No. 4,340,583, Jul. 29, 1982, incorporated herein by reference.

The abrasive in the compositions described herein is present at a level of from about 6% to about 70%, preferably from about 15% to about 35% when the composition is a toothpaste. Higher levels, as high as 95%, may be used if the composition is a toothpowder.

Optionally, the compositions of the present invention may further include a surfactant. Suitable surfactants include those selected from the group consisting of sarcosinate surfactants, isethionate surfactants and taurate surfactants. Preferred for use herein are alkali metal or ammonium salts of these surfactants. Most preferred herein are the sodium and potassium salts of the following: lauroyl sarcosinate, myristoyl sarcosinate, palmitoyl sarcosinate, stearoyl sarcosinate and oleoyl sarcosinate.

This surfactant can be present in the compositions of the present invention from about 0.1% to about 2.5%, preferably from about 0.3% to about 2.5% and most preferably from about 0.5% to about 2.0% by weight of the total composition.

Other suitable compatible surfactants can optionally be used along with the sarcosinate surfactant in the compositions of the present invention. Suitable optional surfactants are described more fully in U.S. Pat. No. 3,959,458, May 25, 1976 to Agricola et al.; U.S. Pat. No. 3,937,807, Feb. 10, 1976 to Haefele; and U.S. Pat. No. 4,051,234, Sep. 27, 1988 to Gieske et al. These patents are incorporated herein by reference.

Preferred anionic surfactants useful herein include the water-soluble salts of alkyl sulfates having from 10 to 18 carbon atoms in the alkyl radical and the water-soluble salts of sulfonated monoglycerides of fatty acids having from 10 to 18 carbon atoms. Sodium lauryl sulfate and sodium coconut monoglyceride sulfonates are examples of anionic surfactants of this type. Mixtures of anionic surfactants can also be utilized.

Preferred cationic surfactants useful in the present invention can be broadly defined as derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421, Oct. 20, 1970, to Briner et al., herein incorporated by reference, where said quaternary ammonium fluorides have detergent properties. Certain cationic surfactants can also act as germicides in the compositions disclosed herein. Cationic surfactants such as chlorhexadine, although suitable for use in the current invention, are not preferred due to their capacity to stain the oral cavity's hard tissues. Persons skilled in the art are aware of this possibility and should incorporate cationic surfactants only with this limitation in mind.

Preferred nonionic surfactants that can be used in the compositions of the present invention can be broadly defined as compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Preferred zwitterionic synthetic surfactants useful in the present invention can be broadly described as derivatives of aliphatic quaternary ammonium, phosphornium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate.

Preferred betaine surfactants are disclosed in U.S. Pat. No. 5,180,577 to Polefka et al., issued Jan. 19, 1993. Typical alkyl dimethyl betaines include decyl betaine or 2-(N-decyl-N,N-dimethylammonio) acetate, coco betaine or 2-(N-coc-N, N-dimethyl ammonio) acetate, myristyl betaine, palmityl betaine, lauryl betaine, cetyl betaine, cetyl betaine, stearyl betaine, etc. The amidobetaines are exemplified by cocoamidoethyl betaine, cocoamidopropyl betaine, lauramidopropyl betaine and the like. The betaines of choice are preferably the cocoamidopropyl betaine and, more preferably, the lauramido propyl betaine.

In preparing toothpastes, it is necessary to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, xanthan gun, gum arabic, and gum tragacanth can also be used. Thickening agents in an amount from 0.5% to 5.0% by weight of the total composition can be used.

Also desirable for inclusion in the compositions of the present invention are other stannous salts such as stannous gluconate and antimicrobials such as quaternary ammonium salts, such as cetyl pyridinium chloride and tetradecylethyl pyridinium chloride, bis-biquanide salts, nonionic anti microbial salts and flavor oils. Such agents are disclosed in U.S. Pat. No. 2,946,725, Jul. 26, 1960, to Norris et al. and U.S. Pat. No. 4,051,234, Sep. 27, 1977 to Gieske et al., incorporated herein by reference. Other optional components include buffering agents, bicarbonates, peroxides, nitrate salts such as sodium and potassium nitrate. These agents, if present, are included at levels of from about 0.01% to about 30%.

Non-cationic water insoluble agents such as triclosan are additionally useful as optional components of the present invention. Such materials are disclosed in U.S. Pat. No. 4,022,889, to Vinson et al., incorporated herein by reference in its entirety.

The compositions of the present invention can also incorporate a flavoring agent or a mixture of compatible flavoring agents. Such flavoring agents are well known in the art. Those flavoring agents most suitable for use in the present invention include: anise, cassia, clove, dihydroanethole, estragole, eucalyptol, menthol, methyl salicylicate, peppermint, oxanone, phenyl ethyl alcohol, sweet birch, eugenol, spearmint, cinnamic aldehyde, menthone, alpha-ionone, ethyl vanillin, limonene, isoamylacetate, benzaldehyde, thymol, ethylbutyrate and many others. These additional, or further optional, flavoring agents comprise from about 0.01% to about 5.0%, preferably from about 0.05% to about 2.0% and most preferably from about 0.1% to about 1.0% of the herein described composition.

Other optional components include, but are not limited to: coloring agents; sweeteners, including saccharin, dextrose, levulose, cyclamate and aspartate, along with many others; buffering systems such as benzoic acid and sodium benzoate, citric acid and sodium citrate, bicarbonates, peroxides, nitrate salts such as sodium and potassium nitrate and any other buffering system compatible with the invention's herein described essential components. These agents, if present, are included at levels of from about 0.01% to about 30%. Another optional component of the present invention is ethyl alcohol. Ethyl alcohol provides several functions when combined in the compositions of the present invention. Its inclusion can be, but is not limited to use as an additional antibacterial or as an astringent. Ethyl alcohol can be incorporated in the present invention at a level of less than about 40%, preferably less than about 10% and most preferably in concentrations of less than about 2%. These and other optional components are further described in U.S. Pat. No. 5,004,597, Apr. 2, 1991 to Majeti; U.S. Pat. No. 4,885,155, Dec. 5, 1989 to Parran, Jr. et al.; U.S. Pat. No. 3,959,458, May 25, 1976 to Agricola et al. and U.S. Pat. No. 3,937,807, Feb. 10, 1976 to Haefele, all being incorporated herein by reference.

Another preferred embodiment of the present invention is a mouthwash composition. The mouthrinse compositions of the present invention are preferably clear. By "clear" as used herein does not mean colorless, but means substantially lacking the presence of particles of sufficient size to scatter visible light as detected visually. Conventional mouthwash composition components can comprise the carrier for the agents of the present invention. Mouthwashes generally comprise from about 20:1 to about 2:1 of a water/ethyl alcohol solution or be alcohol free and preferably other ingredients such as flavor, sweeteners, humectants and sudsing agents such as those mentioned above for dentifrices. The humectants, such as glycerin and sorbitol give a moist feel to the mouth. Generally, on a weight basis the mouthwashes of the invention comprise 5% to 60% (preferably 5% to 20%) ethyl alcohol, 0% to 20% (preferably 5% to 20%) of a humectant, 0% to 2% (preferably 0.01% to 1.0%) emulsifying agents, 0% to 0.5% (preferably 0.005% to 0.06%) sweetening agent such as saccharin, 0% to 0.3% (preferably 0.03% to 0.3%) flavoring agent, and the balance water. Other optional components described herein earlier for use in toothpaste products are also useful in the mouthwash composition.

Suitable lozenge and chewing gum formulations are disclosed in U.S. Pat. No. 4,083,955, Apr. 11, 1978 to Grabenstetter, incorporated herein by reference in its entirety.

The pH of the present compositions and/or the pH in the mouth can be any pH which is safe for the mouth's hard and soft tissues. Such pH's are generally from about 3 to about 10, preferably from about 4 to about 8. Buffers may be added to maintain this pH. Such buffers should, however, not complex with copper ions in a manner such that the functioning of the compositions of this invention is hindered.

A method of manufacture for the present compositions is found in the examples.

COMPOSITION USE

The present compositions are used in a conventional manner wherein the amounts of product are what users generally use.

The following examples further describe and demonstrate preferred embodiments within the scope of the present invention. The examples are given solely for illustration and are not to be construed as limitations of this invention as many variations thereof are possible without departing from the spirit and scope thereof.

EXAMPLES 1–4

Given below are four dentifrice examples representative of the present invention.

| Component | Weight % Ex. 1 | Ex. 2 | Ex. 3 | Ex. 4 |
|---|---|---|---|---|
| Sorbitol (70% Solution) | 55.799 | 43.549 | 27.049 | 11.977 |
| Glycerine | — | — | — | 5.000 |
| Glycine | 0.218 | 0.218 | 0.218 | 0.290 |
| Copper (II) Sulfate $5H_2O$ | 0.360 | 0.360 | 0.360 | 0.360 |
| Sodium Fluoride | 0.243 | 0.243 | 0.243 | 0.243 |
| Saccharin | 0.130 | 0.130 | 0.130 | 0.130 |
| Titanium Dioxide | 0.525 | 0.525 | 0.525 | 0.525 |
| Xylitol | 2.000 | 10.000 | 20.000 | 25.000 |
| Silica | 20.000 | 20.000 | 20.000 | 20.000 |
| Carboxy Methyl Cellulose | 0.350 | 1.100 | 1.100 | 1.100 |
| Xanthan Gum | 0.475 | 0.475 | 0.475 | 0.475 |
| Flavor | 0.900 | 0.900 | 0.900 | 0.900 |
| Sodium Alkyl Sulfate (28% Solution) | 4.000 | — | 4.000 | 4.000 |
| Sodium Lauroyl Sarcosinate (28% Solution) | — | 4.000 | — | — |
| Water | 15.000 | 18.500 | 25.000 | 30.000 |

*Carboxyvinyl polymer offered by B.F. Goodrich Company.

EXAMPLES 5–8

Given below are four rinse examples representative of the present invention.

| Component | Weight % Ex. 5 | Ex. 6 | Ex. 7 | Ex. 8 |
|---|---|---|---|---|
| Undenatured Alcohol | 16.250 | 16.250 | 16.250 | 11.250 |
| Polysorbate 80* | 0.120 | 0.120 | 0.120 | 0.120 |

-continued

| Component | Weight % Ex. 5 | Ex. 6 | Ex. 7 | Ex. 8 |
|---|---|---|---|---|
| Glycerine | 6.000 | 6.000 | 6.000 | 10.000 |
| Glycine | 0.060 | 0.150 | 0.080 | 0.060 |
| Copper (II) Sulfate-5H$_2$O | 0.100 | 0.200 | 0.100 | 0.100 |
| Saccharin | 0.060 | 0.060 | 0.060 | 0.060 |
| Flavor | 0.150 | 0.100 | 0.150 | 0.120 |
| Xylitol | 5.000 | 10.000 | 20.000 | 25.000 |
| Water | 72.260 | 67.120 | 57.240 | 53.290 |

*Polyoxyethylene (20) sorbitan monooleate.

EXAMPLE 9

| Component | Weight % |
|---|---|
| Mannitol | 10.000 |
| Starch | 17.500 |
| Glycine | 13.600 |
| Copper (II) Sulfate .5H$_2$O | 0.007 |
| Saccharin | 0.01 |
| Xylitol | 26.000 |
| Flavor | 1.50 |
| Corn Syrup | 31.383 |

EXAMPLES 10–13

Given below is a chewing gum example of the present invention.

| Component | Weight % Ex. 10 | Ex. 11 | Ex. 12 | Ex. 13 |
|---|---|---|---|---|
| Sorbitol-Crystaline | 33.145 | 33.060 | 33.133 | — |
| Sorbitol Solution 70% | 15.000 | 15.000 | 15.000 | 15.000 |
| Xylitol | 20.000 | 20.000 | 20.000 | 53.145 |
| Copper (II) Sulfate-5H$_2$O | 0.039 | 0.080 | 0.039 | 0.039 |
| Glycine | 0.028 | 0.060 | 0.040 | 0.028 |
| Trisodium Phosphate | 0.088 | 0.100 | 0.088 | 0.088 |
| Gum Base* | 25.000 | 25.000 | 25.000 | 25.000 |
| Glycerin | 5.000 | 5.000 | 5.000 | 5.000 |
| Flavor | 1.700 | 1.700 | 1.700 | 1.700 |

*30 parts Estergum/45 parts Coumorone Resin/15 parts Dry Latex.

What is claimed is:

1. An oral mouthrinse composition effective against diseases of the oral cavity comprising:

(a) from about 20% to about 70% of xylitol;

(b) a safe and effective amount of copper bis-glycinate; and (c) a pharmaceutically acceptable carrier.

2. A composition according to claim 1 wherein the ratio xylitol to copper bis-glycinate is from about 10,000 to 1 to about 1 to 10 and wherein said composition further comprises an additional monosaccharide, polyhydric alcohol selected from the group consisting of sorbitol, mannitol or mixtures thereof.

3. A composition according to claim 2 wherein the xylitol is present at a level of from about 0.05% to about 80%.

4. A composition according to claim 3 wherein the concentration of copper bis-glycinate is sufficient to provide from about 1 to about 8000 parts per million copper ions.

5. A composition according to claim 4 which is in the form of a mouthrinse.

6. A composition according to claim 5 which further comprises a humectant.

7. A method of preventing and treating diseases of the oral cavity by applying to said cavity a safe and effective amount of a composition according to claim 1.

8. A method of preventing and treating diseases of the oral cavity by applying to said cavity a safe and effective amount of a composition according to claim 4.

9. A method of preventing and treating diseases of the oral cavity by applying to said cavity a safe and effective amount of a composition according to claim 5.

* * * * *